United States Patent
Ho et al.

(10) Patent No.: US 9,468,403 B2
(45) Date of Patent: Oct. 18, 2016

(54) SINGLE-BODY UNIT FOR PULSE OXIMETER CALIBRATION

(71) Applicant: Hong Kong Applied Science and Technology Research Institute Company Limited, Hong Kong (HK)

(72) Inventors: Wing Yan Ho, Hong Kong (HK); Ngok Man Sze, Hong Kong (HK); Lut Hey Chu, Hong Kong (HK)

(73) Assignee: Hong Kong Applied Science and Technology Research Institute Company Limited, Shatin (HK)

( * ) Notice: Subject to any disclaimer, the term of this patent is extended or adjusted under 35 U.S.C. 154(b) by 310 days.

(21) Appl. No.: 14/156,406

(22) Filed: Jan. 15, 2014

(65) Prior Publication Data

US 2015/0196235 A1    Jul. 16, 2015

(51) Int. Cl.
| | | |
|---|---|---|
| A61B 5/1455 | (2006.01) | |
| A61B 5/1495 | (2006.01) | |
| A61B 5/00 | (2006.01) | |
| A61B 5/024 | (2006.01) | |

(52) U.S. Cl.
CPC ......... A61B 5/1495 (2013.01); A61B 5/14552 (2013.01); A61B 5/02433 (2013.01); A61B 5/6816 (2013.01); A61B 5/6823 (2013.01); A61B 5/6826 (2013.01); A61B 2562/0233 (2013.01)

(58) Field of Classification Search
CPC .............. A61B 5/1495; A61B 5/1455; A61B 5/14551; A61B 6/583; A61B 2560/0233
See application file for complete search history.

(56) References Cited

U.S. PATENT DOCUMENTS

| | | | | |
|---|---|---|---|---|
| 4,968,137 A | * | 11/1990 | Yount | A61B 5/1495 600/323 |
| 5,166,517 A | | 11/1992 | Volgyesi | |
| 5,891,730 A | | 4/1999 | Li et al. | |
| 6,400,973 B1 | * | 6/2002 | Winter | A61B 5/1495 600/323 |
| 7,057,164 B2 | * | 6/2006 | Springsteen | G01N 21/278 250/252.1 |
| 7,748,252 B2 | * | 7/2010 | Wieringa | A61B 5/0059 73/1.86 |
| 2015/0164463 A1 | * | 6/2015 | Oraevsky | A61B 5/0095 73/866.4 |

FOREIGN PATENT DOCUMENTS

| | | |
|---|---|---|
| CN | 1836632 A | 9/2006 |
| CN | 1864629 A | 11/2006 |

* cited by examiner

*Primary Examiner* — Eric Winakur
(74) *Attorney, Agent, or Firm* — Norton Rose Fulbright US LLP

(57) ABSTRACT

An all-solid, single-body unit for calibrating a pulse oximeter that uses probe light beams is provided. A bulk of the unit is substantially composed of a mixture of materials comprising one or more polymer materials that form a flexible solid medium for the bulk of the unit, one or more scattering materials for scattering the probe light beams, and one or more dye materials for attenuating the probe light beams. The flexible solid medium enables a pulsatile rhythmic train of action force received by the unit to be transmitted in the unit during calibrating the pulse oximeter for substantially emulating change of absorbance characteristics of the probe light beams due to pulsing arterial blood. The scattering materials and the dye materials are localized in the flexible solid medium, enabling the unit to be used in calibrating the pulse oximeter without a need for an additional device for further emulation.

19 Claims, 3 Drawing Sheets

TABLE 1. Materials used in forming the bulk of a single-body unit.

| Material | Preferred range of weight percentage | Examples of material |
|---|---|---|
| Polymer material(s) | 70% to 99.998% | rubber, polypropylene, polyethylene, silicone (KER2500AB, KER2600AB, KER2700AB, LX251AB, LX287AB, LX280AB, and a combination thereof) |
| Scattering material(s) | 0.001% to 20% | titanium dioxide ($TiO_2$), zinc oxide (ZnO), aluminium oxide ($Al_2O_3$), silica, epoxy particles, microspheres or nanoparticles |
| Dye material(s) | 0.001% to 10% | ABS668, ABS659, ABS654, ABS647B, ABS642, IRA980BT, IRA955, IRA945T, IRA931, IRA908 |

FIG. 1

SINGLE-BODY UNIT FOR PULSE OXIMETER CALIBRATION

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to a device configured to be used in calibrating a pulse oximeter. In particular, the present invention relates to this device realized as a single-body unit.

BACKGROUND

A pulse oximeter is a sensing device for non-invasive measurement of a person's arterial-blood oxygen saturation level. The measurement is done by measuring absorbances of light beams having pre-determined wavelengths after the light beams travel through or are reflected by a pre-determined part of the person's body. Hereinafter, a light beam directed to the pre-determined part of the body for absorbance measurement is referred to as a probe light beam. For a transmissive oximeter, the probe light beams are usually directed to one side of a thin section of the body such as a finger, a palm or an earlobe, and light sensors are used to measure intensities of the light beams that exit this thin section from the opposite side. For a reflective oximeter, the probe light beams may be directed to the skin of a foot, forehead or chest, and photosensors are used to detect the reflected light beams. Typically, two pre-determined wavelengths of 660 nm and 940 nm are used for the probe light beams of the pulse oximeter. The probe light beam having a wavelength of 660 nm is visible and is red light while it is infrared (IR) light for the light beam of 940 nm in wavelength. For background details on a pulse oximeter and its operational principle, refer to J. S. GRAVENSTEIN, *Gas monitoring and pulse oximetry*, Butterworth-Heinemann Limited, 1990, the disclosure of which is incorporated by reference herein.

It is sometimes required to calibrate a pulse oximeter, for example, to check its accuracy before doing measurement for a person or a patient. A calibrator for calibrating the pulse oximeter is used. One requirement of the calibrator is to emulate absorbance characteristics of the probe light beams propagated in the pre-determined part of human body by replicating absorption behavior of each of the probe light beams when the probe light beams encounters human tissues, blood, bones, etc. in the aforementioned part of body. Another requirement is to emulate change of absorbance caused by pulsing arterial blood and experienced by each of the probe light beams when the probe light beams propagate in the pre-determined part of body.

In U.S. Pat. No. 5,166,517, a manually operable calibrator for checking the accuracy of a pulse oximeter has a layered structure, where the pulse oximeter that can be calibrated by this calibrator is a transmissive oximeter. The calibrator comprises a specially prepared liquid and a resiliently flexible displaceable member adjacent to the liquid. The liquid is prepared for emulating absorption behavior of probe light beams traveled in the pre-determined body part. By manually pumping the liquid into and out of the displaceable member in a rhythmic manner, absorbance change due to pulsing arterial blood is emulated. One disadvantage of the calibrator is that its layered structure increases manufacturing costs but lowers the calibrator reliability due to involvement of a plurality of components. Another disadvantage is that liquid is involved, increasing difficulty in handling and in storage. Liquid media are also used in other calibrators, such as the one disclosed in China Patent Application Publication No. 1,864,629.

China Patent Application Publication No. 1,836,632, addressing an issue that existing calibrators in the market easily lead to the over-driven problem during calibration, discloses a light scattering medium in an attempt to solve this problem. The light scattering medium is made of epoxy resin and is incorporated with a selected, preferred volume percentage of scattering materials. When this light scattering medium is used in an oximeter calibrator, the resultant calibrator will have a layered structure with a number of components. The involvement of a number of components increases manufacturing costs and reduces the calibrator reliability.

There is a need in the art for a calibrator having a simple structure realized by minimal components without involving any liquid medium. It is desirable if the calibrator can be used for calibrating both transmissive oximeters and reflective oximeters.

SUMMARY OF THE INVENTION

The present invention provides a single-body unit configured for use in calibrating a pulse oximeter that uses probe light beams having pre-determined wavelengths. The pulse oximeter may be a transmissive oximeter or a reflective oximeter. A bulk of the single-body unit is substantially composed of a mixture of materials. The mixture of materials comprises one or more polymer materials that form a flexible solid medium for the bulk of the single-body unit, one or more scattering materials for scattering the probe light beams, and one or more dye materials for attenuating the probe light beams. The flexible solid medium is configured to enable a pulsatile rhythmic train of action force received by the single-body unit to be transmitted in the unit during calibrating the pulse oximeter. The one or more scattering materials and the one or more dye materials are used for substantially emulating scattering behavior and absorption behavior, respectively, of the probe light beams when propagated in a pre-determined part of human body. In addition, the one or more scattering materials and the one or more dye materials are localized in the flexible solid medium. Thereby, the single-body unit is usable in calibrating the pulse oximeter without a need for an additional device to further emulate either scattering behavior or absorption behavior of any of the probe light beams propagated in the pre-determined part of human body, as well as without a need to involve any liquid medium.

Advantageously, the one or more polymer materials, the one or more scattering materials and the one or more dye materials are substantially-uniformly dispersed at least in a functional region of the flexible solid medium where the functional region is configured for interacting with the probe light beams. It follows that an absorbance characteristic of each of the probe light beams when the probe light beams propagate in the functional region is predictable or obtainable. Preferably, the one or more polymer materials, the one or more scattering materials and the one or more dye materials are substantially-uniformly dispersed in the entire bulk of the single-body unit. In addition, the one or more polymer materials are formulated to configure the flexible solid medium such that the flexible solid medium translates the pulsatile rhythmic train of action force into a rhythmic, temporally-coherent variation of the probe light beams' absorbance characteristics. Thereby, it substantially emulates change of absorbance caused by pulsing arterial blood and experienced by each of the probe light beams propagated in the pre-determined part of human body.

In one option, the flexible solid medium is configured to distribute the pulsatile rhythmic train of action force substantially-evenly throughout the single-body unit during calibrating the pulse oximeter. In another option, the flexible solid medium has a hardness level selected such that the pulsatile rhythmic train of action force generated by any stimulation according to a pre-determined set of stimulation conditions is transmittable throughout the single-body unit.

Other aspects of the present invention are disclosed as illustrated by the embodiments hereinafter.

BRIEF DESCRIPTION OF THE DRAWINGS

FIG. 1 provides a table listing the materials, preferred ranges of weight percentage and examples of these materials as used in forming a single-body unit in accordance with an embodiment of the present invention.

DETAILED DESCRIPTION OF THE INVENTION

Figure 2:
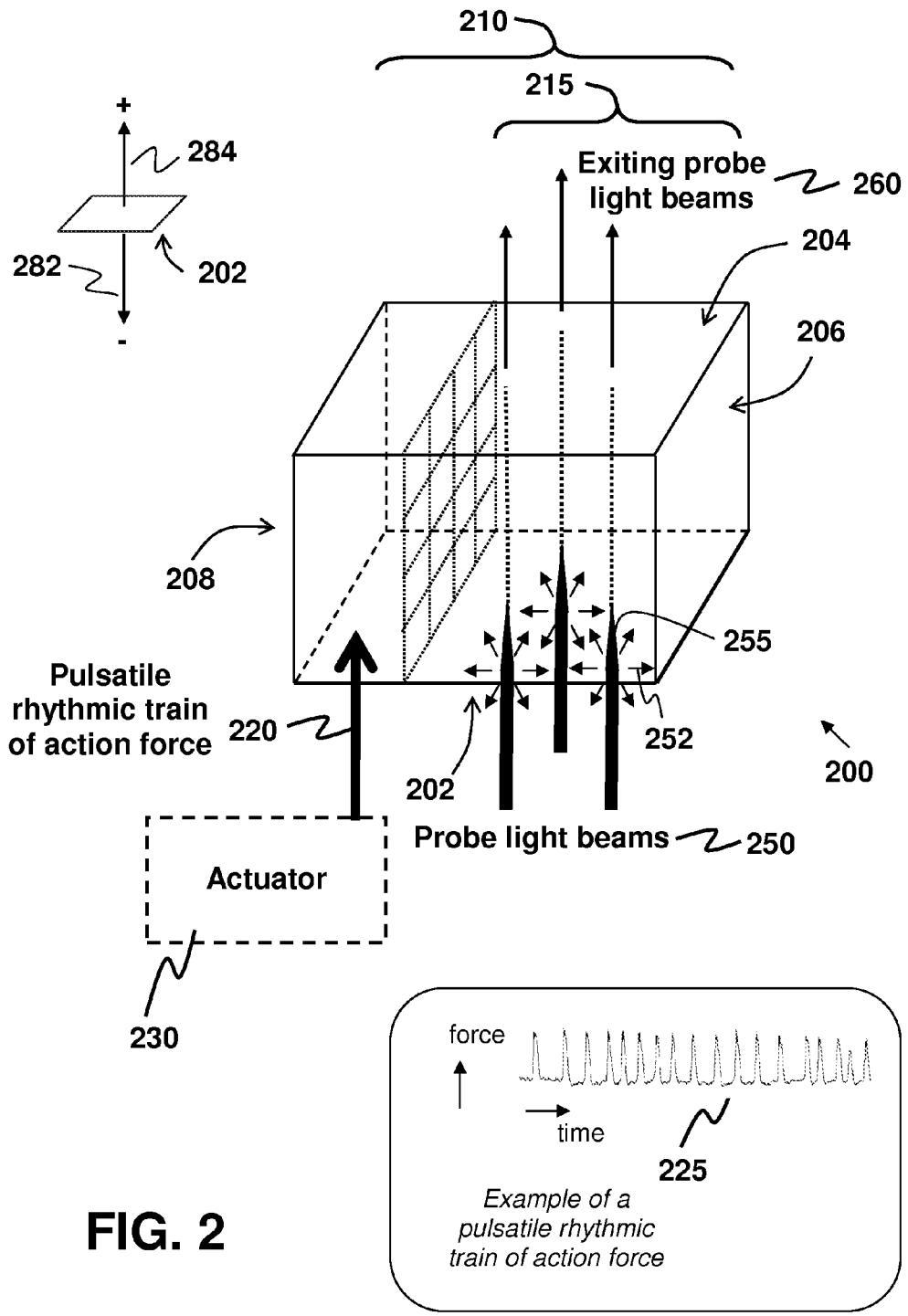
FIG. 2 depicts a single-body unit in accordance with an embodiment of the present invention, together with an illustration of absorption and scattering of probe light beams inside the unit and an application of a pulsatile rhythmic train of action force to the single-body unit, where a pulse oximeter under calibration is a transmissive oximeter.

As used herein, "absorption" of light traveling in a medium includes the concept of partial absorption of the light during traveling in the medium. That is, "absorption" of the light includes not only the case that the light is totally absorbed in the medium, but also a wider range of cases where the light is partially absorbed after passing through the medium. Whether partial or total absorption occurs depends on the light radiation absorption characteristic of the medium.

An aspect of the present invention is to provide an all-solid, single-body unit configured to be used in calibrating a pulse oximeter that uses probe light beams having pre-determined wavelengths. In many practical applications, the single-body unit is configured for only two pre-determined wavelengths, one of which is a red light having a wavelength in a range from 600 nm to 780 nm and another one of which is an IR light with a wavelength inclusively within 780 nm to 1100 nm. Usually, the two wavelengths are selected to be 660 nm and 940 nm, both of which are often adopted by pulse oximeters.

As used herein in the specification and the appended claims, "a flexible solid medium" is a non-rigid solid matter mechanically configured such that a rhythmic train of pulsatile force applied to one end or one side of the solid matter is able to propagate throughout the solid matter by minute deformation to local parts of the solid matter during propagation. Nevertheless, it is possible that the force is attenuated during the course of propagation by partial absorption of the force at the local parts.

Herein in the specification and in the appended claims, a "bulk" of the single-body unit refers to a main part of the unit where the main part of the body forms a self-contained part functionally configured for pulse-oximeter calibration. It follows that, for example, if the single-body unit has a protective layer thereon only for mechanically protecting the unit, then the protective layer is excluded from the bulk of the single-body unit.

A bulk of the single-body unit is substantially composed of a mixture of materials comprising one or more polymer materials, one or more scattering materials, and one or more dye materials. The one or more polymer materials form a flexible solid medium for the bulk of the single-body unit. The one or more scattering materials are used for scattering the probe light beams in order to substantially emulate scattering behavior of the probe light beams when propagated in a pre-determined part of human body. As an example, the single-body unit may be configured for the pre-determined body part that is a finger. Other examples of the pre-determined body part include a palm, an earlobe, a foot, and other parts of the body such as chest and forehead. In general, each of the scattering materials can be an inorganic, organic or organometallic compound with any suitable crystal form, particle size and refractive index. The one or more dye materials are used for attenuating the probe light beams so as to substantially emulate absorption behavior of the probe light beams when the probe light beams propagate in the pre-determined part of human body. If more than one dye materials are used, different dye materials are usually selected with mutually substantially-different light radiation absorption characteristics in order to simplify formulating the dye materials for sufficiently emulating the aforementioned absorption behavior. FIG. 1 provides a table listing examples of the materials used in forming the single-body unit, and preferred ranges of weight percentage of the materials (Table 1). Since the pulse oximeter is to measure the saturation of peripheral oxygen ($SpO_2$) level of a person, the single-body unit is intended to provide emulation for a particular $SpO_2$ level. A wide range of $SpO_2$ levels ranging from 0% to 100% can be obtained by fine tuning (1) concentrations of the one or more scattering materials and of the one or more dye materials, and (2) corresponding ratios of the dye materials if a plurality of dye materials is used.

Furthermore, the flexible solid medium is configured to transmit a pulsatile rhythmic train of action force throughout the single-body unit when the unit receives this train of action force during calibrating the pulse oximeter. In one option, the flexible solid medium is further configured to distribute this train of action force substantially-evenly throughout the single-body unit. In another option, the flexible solid medium is additionally configured to have a hardness level selected such that the pulsatile rhythmic train of action force generated by any stimulation according to a pre-determined set of stimulation conditions is transmittable throughout the single-body unit. The pulsatile rhythmic train of force, when applied to the single-body unit, synchronously produces a pulsatile rhythmic resilience to the unit in order to substantially emulate change of absorbance caused by pulsing arterial blood for each of the probe light beams propagating in the pre-determined part of human body.

In particular, the single-body unit as disclosed herein is featured by localizing both the one or more scattering materials and the one or more dye materials in the flexible solid medium. As used herein, a material being localized in the flexible solid medium means that the material is substantially fixed and substantially immobilized in the flexible solid medium. It follows that it is not required to have an additional device to further emulate either scattering behavior or absorption behavior of any of the probe light beams when propagated in the pre-determined part of human body. Hence, calibration of the pulse oximeter can be done by using the single-body unit without a need for the aforementioned additional device. Another advantage of localizing the one or more scattering materials and the one or more dye materials in the flexible solid medium is that no liquid medium is involved.

Forming the flexible solid medium from the one or more polymer materials with an objective of localizing the one or more scattering materials and the one or more dye materials in the flexible solid medium can be performed by a suitable chemical-processing method. For selecting the suitable chemical-processing method, see MEYR KUTZ (ed.), *Applied Plastics Engineering Handbook: Processing and Materials*, Elsevier, 2011, the disclosure of which is incorporated by reference herein.

Preferably, the single-body unit is configured to be used in calibrating the pulse oximeter that is a transmissive oximeter or a reflective oximeter. To achieve this purpose, the unit is configured to transmit and reflect the probe light beams. After the probe light beams are transmitted and reflected in the unit, part of the probe light beams exit the unit in a forward direction, and another part of the probe light beams exit the unit in a backward direction. As used herein, the forward direction and the backward direction are relative to an entry direction of the probe light beams upon entering into the unit and, in particular, if a forward (backward) direction is regarded as a unit vector, the projection of the unit vector in the entry direction has a positive (negative) scalar component. Note that exiting probe light beams traveling in a forward (backward) direction may be received and usable by a transmissive (reflective) oximeter.

FIG. 2 depicts a single-body unit in accordance with an embodiment of the present invention. Although a single-body unit 200 shown in FIG. 2 has a shape of a rectangular cuboid, the present invention is not limited to this shape only. Other shapes that can be advantageously used for practical applications of oximeter calibration, such as a cylindrical shape for emulating a human finger, or a sheet shape with average thickness in a range from 1 mm to 20 mm for fitting with some mechanical design, may be employed.

A bulk 210 of the single-body unit 200 is a flexible solid medium formed by one or more polymer materials. In the bulk 210 of the single-body unit 200, there is a functional region 215 configured for interacting with probe light beams 250. The rest of the bulk 210 other than the functional region 215 serves for other purposes, such as allowing a user to handle the single-body unit 200. At least the functional region 215, which is also in the flexible solid medium, is dispersed with one or more scattering materials and one or more dye materials.

The single-body unit 200 receives the probe light beams 250 from a pulse oximeter for calibration. The probe light beams 250 enter the unit 200 via a first end face 202 thereof. Some light of the probe light beams 250 is scattered by the one or more scattering materials in the functional region 215, as indicated by scattered light 252. The remaining light of the probe light beams 250 is attenuated, or partially absorbed, by the one or more dye materials, as indicated by diminishing-intensity light 255. The remaining light may also be attenuated by the one or more polymer materials, depending on light-absorption properties thereof. After attenuation and scattering, exiting probe light beams 260 leave the single-body unit 200 through a second end face 204. As mentioned above, a pulsatile rhythmic train of action force 220 is applied to the single-body unit 200 during calibration of the pulse oximeter. This train of action force 220 can be applied to any end face (e.g. the first end face 202, the second end face 204, or one of lateral end faces 206, 208) of the unit 200. In FIG. 2, the train of action force 220 is applied to the first end face 202 as an example. FIG. 2 also shows an example 225 of this train of action force 220.

Although not shown in FIG. 2 for simplicity, preferably the unit 200 is configured to guide the train of action force 220 such that this train of action force 220 is applied to the unit 200 with an action-force direction pointing to the functional region 215, where the aforementioned action-force direction is a direction that the pulsatile rhythmic train of action force 220 is applied to the single-body unit 200. A configuration for guiding the train of action force 220 to point to the functional region 215 may be, for example, a mark painted on the unit 200 for indicating a location on which the train of action force 220 is applied.

It is also preferable that the unit 200 is further configured to guide the pulsatile rhythmic train of action force 220 to apply to the unit with the action-force direction substantially parallel to a propagation direction of the probe light beams 250 emitted by the pulse oximeter. As used herein, "a propagation direction of probe light beams emitted by a pulse oximeter" is a representative direction that the probe light beams collectively propagate. Even if all the probe light beams do not propagate in the same direction and produce a cone of light beams, the representative propagation direction can be determined, e.g., by identifying a direction along which luminance of a light beam from the cone of light beams is maximum over the cone.

Figure 3:
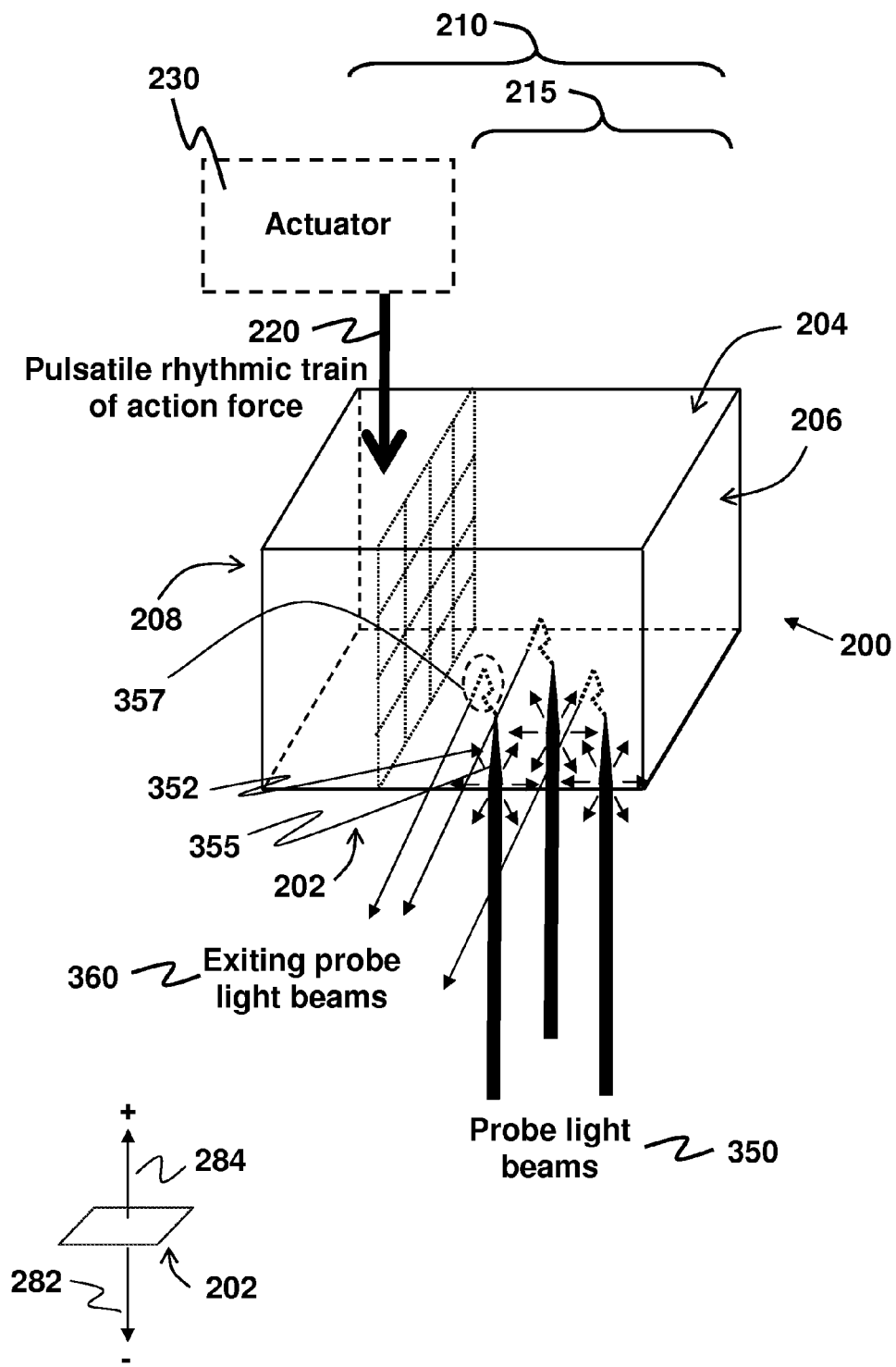
FIG. 3 also depicts the single-body unit of FIG. 2, but the pulse oximeter under calibration is a reflective oximeter.

In FIG. 2, the first end face 202 and the second end face 204 are opposite to each other so that the pulse oximeter under calibration is a transmissive one. The single-body unit 200 is also applicable to a reflective oximeter. FIG. 3 depicts the situation where the single-body unit 200 is used for calibrating a reflective oximeter. Probe light beams 350 of the reflective oximeter enter into the unit 200 through the first end face 202. The probe light beams 350 are scattered, as indicated by scattered light 352, and also attenuated, as indicated by diminishing-intensity light 355. The probe light beams 350 also undergo multiple scattering, as indicated by a zig-zag light path 357. Some light of the probe light beams 350 after multiple scattering is reflected substantially backward, and leaves the unit 200 via the first end face 202 so that the reflective oximeter receives exiting probe light beams 360 by the same side of the oximeter where the probe light beams 350 are emitted. Similarly, the pulsatile rhythmic train of action force 220 is applied to the single-body unit 200 (on the second end face 204) during calibration of the reflective oximeter.

It is advantageous and highly preferable that the one or more polymer materials, the one or more scattering materials and the one or more dye materials are substantially-uniformly dispersed at least in the functional region 215. By this arrangement of substantially uniform dispersion, an absorbance characteristic of each of the probe light beams 250 propagated in the functional region 215 is predictable or obtainable. Optionally, the one or more polymer materials, the one or more scattering materials and the one or more dye materials are substantially-uniformly dispersed in the entire bulk 210 of the single-body unit 200. It is also advantageous and desirable to configure the flexible solid medium such that the flexible solid medium translates the pulsatile rhythmic train of action force 220 into a rhythmic, temporally-coherent variation of absorbance characteristics of all the probe light beams 250. The absorbance-characteristic variation among all probe light beams being temporally-coherent means that an absorbance-characteristic variation of one probe light beam over time is time-synchronized with that of another probe light beam. This temporally-coherent variation is achievable in that the one or more scattering materials and the one or more dye materials are localized in the flexible solid medium so that a minute deformation to the flexible solid medium by the pulsatile rhythmic train of action force 220 changes local concentrations of the one or more scattering materials and of the one or more dye materials synchronously and coherently. Thereby, change of absorbance caused by pulsing arterial blood and experienced by each of the probe light beams 250 when the probe light beams 250 propagate in a pre-determined part of human body is substantially emulated.

The pulsatile rhythmic train of action force 220 may be generated by an actuator 230. A pulse-oximeter calibrator is realizable by including the single-body unit 200 and the actuator 230. In one embodiment, the actuator 230 generates and applies this train of action force 220 in a substantially vertical direction 284 to the single-body unit 200 on the first end face 202 or the second end face 204 to thereby produce the rhythmic, temporally-coherent variation of the absorbance characteristics of all the probe light beams 250.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. An apparatus comprising:
   a single-body unit configured to calibrate a pulse oximeter that uses probe light beams having pre-determined wavelengths to measure the saturation of peripheral oxygen (SpO$_2$) level of a pre-determined human body part, wherein the single-body unit is formed from a mixture of materials, the mixture of materials comprising:
   one or more polymer materials that form a flexible solid medium configured to transmit a pulsatile rhythmic train of action force received by the single-body unit during calibration of the pulse oximeter;
   one or more scattering materials to scatter the probe light beams, wherein the scattering of the probe light beams by the one or more scattering materials during the calibration of the use oximeter emulates scattering behavior of the probe light beams when propagated in the pre-determined human body part; and
   one or more dye materials to attenuate the probe light beams, wherein the attenuation of the probe light beams by the one or more dye materials during the calibration of the pulse oximeter emulates to absorption behavior of the probe light beams when propagated in the pre-determined human body part,
   wherein the one or more polymer materials form a bulk of the single-body unit, wherein each of the one or more scattering materials and each of the one or more dye materials are substantially-uniformly dispersed in the entire single-body unit, and wherein the one or more polymer materials, the one or more scattering materials, and the one or more dye materials are selected such that the mixture of materials forming the single-body unit emulates a particular SpO$_2$ level during the calibration of the pulse oximeter, the particular SpO$_2$ level corresponding to an expected SpO$_2$ level for the pre-determined human body part when measured using the pulse oximeter.

2. The apparatus of claim 1, wherein the one or more polymer materials are formulated to configure the flexible solid medium such that the flexible solid medium translates the pulsatile rhythmic train of action force into a rhythmic, temporally-coherent variation of the probe light beams' absorbance characteristics to substantially emulate change of absorbance caused by pulsing arterial blood and experienced by each of the probe light beams when the probe light beams propagate in the pre-determined human body part.

3. The apparatus of claim 2, further comprising:
   an actuator for generating and applying the pulsatile rhythmic train of action force to the single-body unit.

4. The apparatus of claim 1, wherein the single-body unit is further configured to guide the pulsatile rhythmic train of action force to apply the pulsatile rhythmic train of action force to the single-body unit in an action-force direction.

5. The apparatus of claim 4, wherein the action-force direction is substantially parallel to a propagation direction of the probe light beams emitted by the pulse oximeter.

6. The apparatus of claim 1, wherein the pre-determined human body part is a finger, a palm, an earlobe, a foot, a forehead or a chest.

7. The apparatus of claim 1, wherein 70% to 99.998% of the mixture of materials comprises the one or more polymer materials, wherein 0.001% to 20% of the mixture of materials comprises the one or more scattering materials, and wherein 0.001% to 10% of the mixture of materials comprises the one or more dye materials.

8. The apparatus of claim 1, wherein the one or more polymer materials comprises rubber, polypropylene (PP), polyethylene (PE), silicone or a combination thereof.

9. The apparatus of claim 1, wherein the one or more scattering materials comprises, nanoparticles, titanium dioxide (TiO$_2$), zinc oxide (ZnO), aluminium oxide (Al$_2$O$_3$), silica, epoxy particles, microspheres or a combination thereof.

10. The apparatus of claim 1, wherein the one or more dye materials comprise a plurality of different dye materials, and light radiation absorption characteristics of the different dye materials are mutually substantially-different.

11. The apparatus of claim 1, wherein one of the pre-determined wavelengths is in a range from 600 nm to 780 nm and another one of the pre-determined wavelengths is in a range from 780 nm to 1100 nm.

12. The apparatus of claim 11, further comprising:
   an actuator for generating and applying the pulsatile rhythmic train of action force to the single-body unit.

13. The apparatus of claim 1, wherein the flexible solid medium has a hardness level selected such that the pulsatile rhythmic train of action force generated by any stimulation according to a pre-determined set of stimulation conditions is transmittable throughout the single-body unit.

14. The apparatus of claim 1, wherein the single-body unit is configured to be used in calibrating the pulse oximeter that is a transmissive oximeter or a reflective oximeter.

15. The apparatus of claim 14, further comprising:
   an actuator for generating and applying the pulsatile rhythmic train of action force to the single-body unit.

16. The apparatus of claim 1, wherein the single-body unit is configured to transmit and reflect the probe light beams.

17. The apparatus of claim 16, wherein the single-body unit is configured such that, after the probe light beams are transmitted and reflected in the single-body unit, part of the probe light beams exit the single-body unit in a forward direction relative to an entry direction of the probe light beams upon entering into the single-body unit, and another part of the probe light beams exit the single-body unit in a backward direction relative to the entry direction.

18. The apparatus of claim 1, further comprising:
an actuator for generating and applying the pulsatile rhythmic train of action force to the single-body unit.

19. A method for manufacturing an apparatus configured to calibrate a pulse oximeter, the method comprising:
selecting a plurality of materials for forming a single-body unit configured to calibrate a pulse oximeter that uses probe light beams having pre-determined wavelengths to measure the saturation of peripheral oxygen ($SpO_2$) level of a pre-determined human body part, wherein the plurality of materials comprises one or more polymer materials, one or more scattering materials, and one or more dye materials, wherein the one or more polymer materials, the one or more scattering materials, and the one or more dye materials are selected to configure the single-body unit to emulate a particular $SpO_2$ level during the calibration of the pulse oximeter, the particular $SpO_2$ level corresponding to an expected $SpO_2$ level for the pre-determined human body part when measured using the pulse oximeter;
mixing the plurality of materials to form a mixture of materials; and
forming the single-body unit from the mixture of materials, wherein the one or more polymer materials form a flexible solid medium and account for a bulk of the single-body unit, wherein the flexible solid medium is configured to transmit a pulsatile rhythmic train of action force received by the single-body unit during calibration of the pulse oximeter, wherein the one or more scattering materials are configured to scatter the probe light beams during calibration of the pulse oximeter to emulate scattering behavior of the probe light beams when propagated in the pre-determined human body part, wherein the one or more dye materials are configured to attenuate the probe light beams during calibration of the pulse oximeter to emulate an absorption behavior of the probe light beams when propagated in the pre-determined human body part, and wherein each of the one or more scattering materials and each of the one or more dye materials are substantially-uniformly dispersed in the entire bulk of the single-body unit.

* * * * *